United States Patent [19]
Hulbert

[11] Patent Number: 5,248,442
[45] Date of Patent: Sep. 28, 1993

[54] METHOD AND APPARATUS FOR MEASURING SHADE OF HYDROCYCLONE UNDERFLOW

[75] Inventor: David G. Hulbert, Randburg, South Africa

[73] Assignee: Mintek, Randburg, South Africa

[21] Appl. No.: 744,904

[22] Filed: Aug. 14, 1991

Related U.S. Application Data

[63] Continuation-in-part of Ser. No. 618.088. Nov. 26. 1990. Pat. No. 5.132.024. which is a continuation-in-part of Ser. No. 430.259. Oct. 20. 1989. abandoned.

[30] Foreign Application Priority Data

Jul. 9. 1991 [ZA] South Africa .................. 91/5315

[51] Int. Cl.⁵ .............................. B01D 17/12
[52] U.S. Cl. ........................ 210/740; 73/227; 73/281; 209/211; 209/546; 209/552; 210/87; 210/103; 210/143; 210/741; 241/33; 340/606
[58] Field of Search .............. 73/861.73, 865.9, 281, 73/227; 209/211, 499, 546, 552; 210/87, 90, 103, 143, 512.1, 739, 740, 741, 787; 241/34, 33; 340/606; 364/502, 510, 558

[56] References Cited

U.S. PATENT DOCUMENTS

| | | | |
|---|---|---|---|
| 3,114,510 | 12/1963 | McCarty et al. | 241/34 |
| 3,783,252 | 1/1974 | Putman | 241/34 |
| 4,246,576 | 1/1981 | Grieve et al. | 241/34 |
| 4,441,102 | 4/1984 | Webb | 340/606 |
| 4,670,161 | 6/1987 | Hayatdavoudi | 210/739 |
| 5,132,024 | 7/1992 | Hulbert | 210/739 |

FOREIGN PATENT DOCUMENTS 543410 1/1977 U.S.S.R. ..................... 209/211

Primary Examiner—Joseph W. Drodge
Attorney, Agent, or Firm—Mason, Fenwick & Lawrence

[57] ABSTRACT

A method and means for measuring a characteristic, in particular one associated with particle size, of any of the feed, underflow or overflow streams of a hydrocyclone is provided. Information as to the flowrate and density of the feed stream as well as the angle of flare or other related variable associated with the shape of the underflow stream are fed to processing means which applies a formula or algorithm, which is usually empirically derived, to such information to provide a value of the required characteristic. The characteristic may be related to particle size, particle size distribution in any of the streams or the liquid content or the flowrates of solids or liquids in the underflow or overflow. Measurement apparatus comprising a dedicated hydrocyclone is also provided.

43 Claims, 3 Drawing Sheets

METHOD AND APPARATUS FOR MEASURING SHADE OF HYDROCYCLONE UNDERFLOW

RELATED APPLICATIONS

This application is a continuation-in-part application of U.S. application Ser. No. 07/618,088 filed on Nov. 26, 1990, now U.S. Pat. No. 5,132,024 which was a continuation-in-part of U.S. application Ser. No. 07/430,259 filed on Oct. 20, 1989 now abandoned.

FIELD OF THE INVENTION

This invention relates to a measurement method and apparatus for, or embodying, hydrocyclones, and, more particularly, to a method and apparatus for measuring a characteristic associated with any of the feed, underflow or overflow streams of a hydrocyclone. The characteristic being measured may be related to particle size of solids in any of the streams or to the liquid content or the flowrate of solids, liquid or both in the underflow or overflow streams. Still more particularly the invention relates to a method and apparatus which employ, as one measured variable, a measurement associated with the shape of the underflow stream emanating from a hydrocyclone.

Whilst the invention is primarily concerned with the measurement of characteristics associated with the flow streams of a hydrocyclone in a practical application, it extends also to apparatus which includes a hydrocyclone dedicated to the purpose of measurement and which thus forms part of the measurement apparatus.

BACKGROUND TO THE INVENTION

Hydrocyclones are widely used in the metallurgical industry for the separation of particles in a slurry according to their size and/or density, the particles emerging in one of two streams, namely, the underflow or the overflow.

As is well known, the proper operation of a hydrocyclone depends on a suitable rotational motion of slurry inside the cyclone with a core of air along its axis. This rotational motion is still present in the underflow of a cyclone with the result that the combined axial and angular velocities of the underflow stream cause it to adopt the nature of a spray of nearly conical shape. When a hydrocyclone is overloaded, the rotational motion of the slurry in the cyclone is altered such that the angular velocity of the slurry emerging from the hydrocyclone as an underflow stream is small compared with its axial velocity. This causes the air core to be disturbed and a slender rope-shaped discharge or a blockage to result.

Common on-line measurements used in connection with the operation of hydrocyclones are the flowrate and density of the slurry being fed to the hydrocylone and, in some cases, the inlet pressure of such slurry. The inlet pressure has proved to be of little use in the derivation of additional information because it is highly correlated with the feed flow and density measurements.

The actual shape of the hydrocyclone underflow stream is approximately conical, under normal operating conditions, and has therefore a radius at some distance away from the underflow outlet itself. This radius can be sufficient to characterise the shape of the underflow stream. Alternatively, and more conveniently, the shape can be characterised by the angle of flare of the approximately conical stream. This angle varies continuously with changes in the variables associated with the operation of the hydrocyclone.

This feature of the underflow stream has been used, in the past, to control the operation of a hydrocyclone to some extent, or at least to shut it down or provide an alarm when the shape of an underflow stream corresponds to undesirable operation, such as roping.

Thus, for example, there has been described in U.S. Pat. No. 4,246,576 to Grieve et al a monitor which is, in effect, a transition detector, and which provides an outward indication simply of whether the underflow is "normal" or "abnormal". In effect this monitor simply acts as a switch indicating either of two conditions of the underflow.

U.S. Pat. No. 3,114,510 to McCarthy and Curtis describes another form of underflow monitor which simply determines whether or not the shape (angle) of the underflow is between two limits corresponding to "underload" and "overload". In other words the monitor simply detects whether or not the shape of the underflow is anywhere within a desired operating range, but gives no indication as to where in such operating range.

Applicant has already established that the shape (angle) of the underflow stream over a continuous range between chosen limits, can be used in the control of the operation of a hydrocyclone or, alternatively, a milling circuit embodying a hydrocyclone.

Further research and development has now revealed that use of the shape or angle of the underflow stream of a hydrocyclone can in fact be employed in a method and apparatus for actually measuring characteristics associated with the feed, underflow, or overflow streams of a hydrocyclone and, in particular, in particle size, liquid content, and mass flowrate determinations.

It is, accordingly, the object of this invention to provide a method and means for the measurement of a characteristic of any of the feed, underflow or overflow streams of a hydrocyclone wherein the shape (angle) of the underflow stream is employed as one process input to effect measurement of such a characteristic.

It is another object of this invention to provide measurement apparatus which embodies a hydrocyclone and means for measuring the shape (angle) of the underflow stream.

SUMMARY OF THE INVENTION

In accordance with one aspect of this invention there is provided a method of measuring a characteristic associated with any of the feed, underflow, or overflow streams of a hydrocyclone comprising monitoring the flowrate and density of the feed stream to the hydrocyclone and simultaneously monitoring the angle, fluctuations in angle, or other related variable associated with the shape of the underflow stream over a substantially continuous operating range, and processing information derived from the monitoring of the flowrate and density of the feed stream and variable associated with the shape of the underflow stream according to a formula or algorithm which is optionally emperically derived, to provide a value of said characteristic.

Further features of this aspect of the invention provide for the characteristic to be one associated with the particle size or size ranges of particles contained in the feed, overflow or underflow streams and more particularly for the characteristic to be the proportion of particles having a size greater than, or less than, a predetermined size; for the variable associated with the shape of the underflow stream to be the radius of the substantially conical underflow stream at a specified distance away from the underflow aperture of the hydrocyclone; and for the measured characteristic t be employed in the control of the operation of the hydrocyclone or a circuit embodying same.

Still further features of the invention provide for the variable associated with the shape of the underflow stream to be monitored using a substantially abrasion resistant element operatively riding on the outer boundary region of the underflow stream; for the abrasion resistant member to be carried at the end of a downwardly extending movable arm or arms; and for the measured characteristic either in the alternative to one associated with particle size, or in addition thereto, to be the solids or liquid content of the underflow or overflow streams or simply the flowrate of a stream itself.

In accordance with a second aspect of this invention there is provided apparatus for measuring a characteristic associated with any of the feed underflow or overflow streams of a hydrocyclone, said apparatus comprising flowrate monitoring means for providing information as to the flowrate of feed material to the hydrocyclone; density monitoring means for providing information as to the density of said feed material underflow monitoring means for monitoring the angle, fluctuations in angle, or other related variable associated with shape or the underflow stream; and processing means for applying a formula or algorithm (optionally emperically derived) to said information to provide a value of said characteristic.

In particular, there may be measured by the method and apparatus of this invention any one or more of the following:

(i) the proportion of material in a hydrocyclone overflow having a particle size less than or greater than a preset value, for example, the proportion of solid material having a particle size of method and means for measuring a characteristic, less than 75 $\mu m$;

(ii) the proportion of fine material in a hydrocyclone underflow, for example having a particle size or less than 10 $\mu m$;

(iii) the solids content of a hydrocyclone underflow as a percentage of the total underflow;

(iv) the flowrate of solids in a hydrocyclone underflow, for example in kilograms per second;

(v) the flowrate of water in a hydrocyclone underflow, for example in kilograms per second; and, (vi) the proportion of solid material in a hydrocyclone feed stream having a particle size above or below a certain value, for example the proportion having a particle size less than say 75 $\mu m$.

Accordingly the invention also provides a particle size monitor which may have a dedicated hydrocyclone forming part of the measurement apparatus itself.

In order that the invention may be more fully understood, a detailed description of one application and various alternatives, now follow with reference to the accompanying drawings.

DETAILED DESCRIPTION WITH REFERENCE TO THE DRAWINGS

Figure 1:
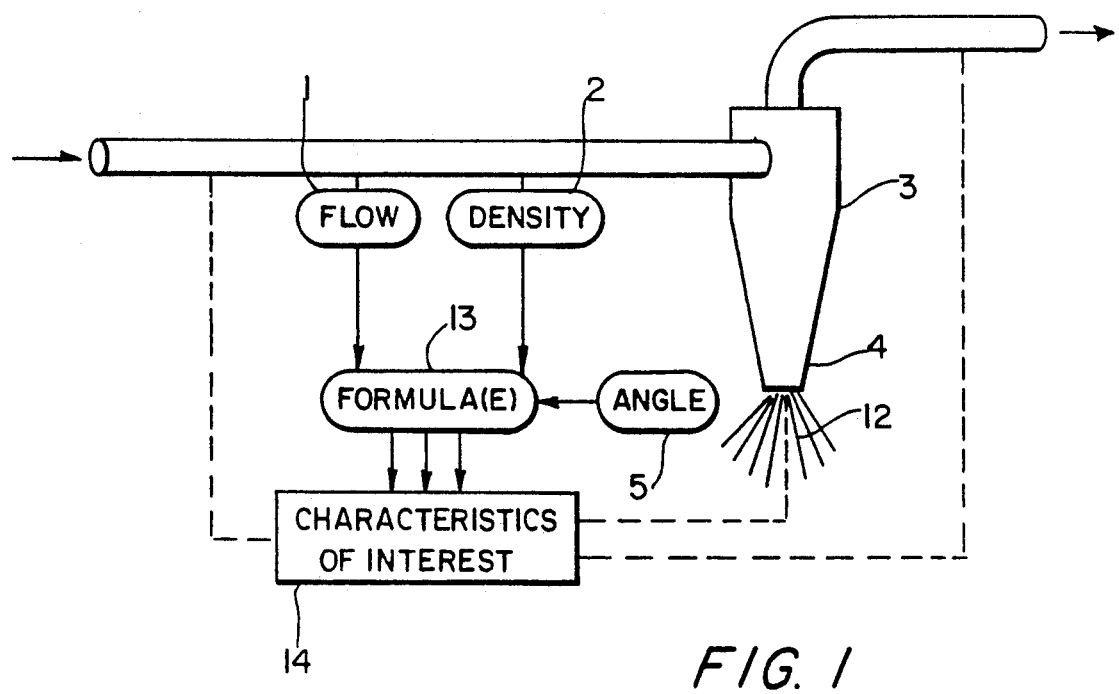
FIG. 1 is a schematic diagram of apparatus according to the invention in one application thereof.

Referring firstly to FIG. 1 there is illustrated, schematically, apparatus according to the invention which was particularly adapted, in this instance, to measure the proportion of solids in the overflow stream of a hydrocyclone having a particle size or less than 75 $\mu m$. The apparatus, in this case, comprised a feed rate flow measurement device 1 and a density measurement device 2 for measuring the density of the feed stream to a hydrocyclone 3.

The hydrocyclone was fitted, at this outlet end 4, with a device 5 for providing information as to the cone angle (or radius) of the underflow stream. The flowrate measurement device 1 and the density measurement device 2 are of any suitable form as are well known in the art and are not further described herein.

Figure 2:
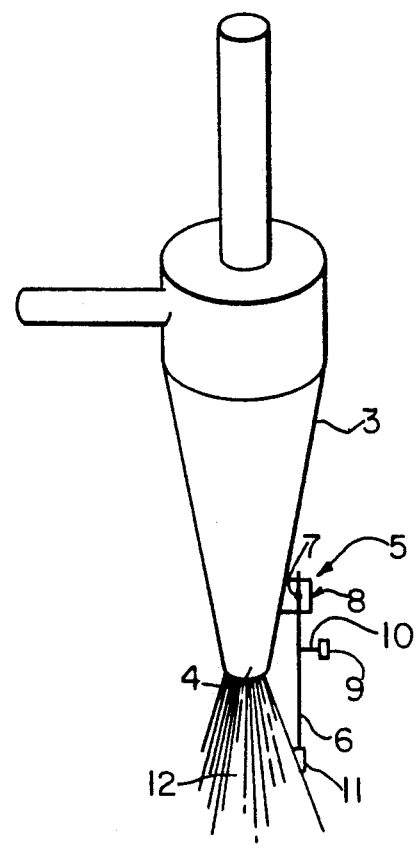
FIG. 2 is a schematic illustration of one means for monitoring the angle of the underflow slurry stream emanating from a hydrocyclone underflow outlet.

The device 5 for measuring the cone angle of the underflow stream could also take many different forms but, in this case, took the simple form illustrated in FIG. 2. In this case, the hydrocyclone outlet 4 was provided with a pivotally mounted, downwardly depending arm 6 mounted towards its upper end on its pivot 7 with which is associated an angle detector 8.

A counterweight 9 is carried on an outwardly projecting intermediate lateral arm 10 and the lowermost end of the downwardly extending arm is provided with an abrasion resistant tip 11.

The tip 11 and counterweight as well as the other design variables of the arm arrangement are such that the abrasion resistant tip rides on the outer boundary of the generally conical shaped outlet stream 12 of slurry at a position spaced downwardly from the underflow outlet 4. The arrangement is such that the angle of the arm provides a measure of the angle of the underflow stream.

Reverting now to FIG. 1, the information generated by the flow measuring device density measuring device 2, and angle measuring device 5, are fed to a processor 13, conveniently in the form of a computer, programmed with a formula or algorithm which is applied to the information in order to provide a measurement of the required characteristic. In this case the characteristic of interest is the proportion of solids having a particle size of less than 75 $\mu m$ in the overflow stream. A recorder 14 was employed to record the outputted information and calculated percentage of particles having a size less than 75 $\mu m$.

Figure 3:
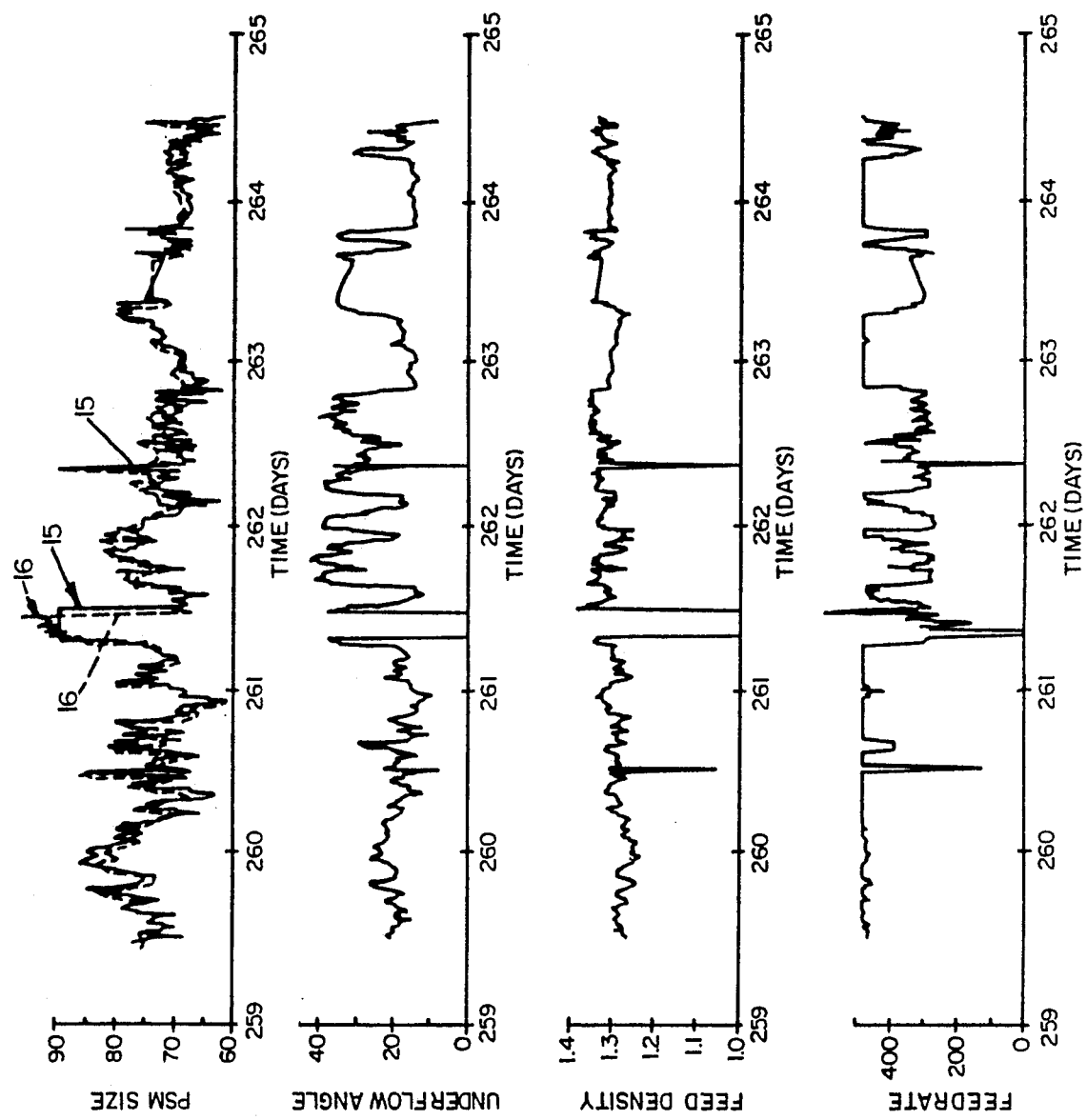
FIG. 3 is a reproduction of a set of recorded charts of certain variables in an industrial milling circuit in which the expedient of this invention was employed to provide a modelled particle size distribution, in particular the percentage of solids having a particle size of less than 75 $\mu m$; and, FIG. 4 is an analogous set of recorded charts showing the best alternative model particle size which applicant was able to achieve without the expedient of this invention.
Figure 4:
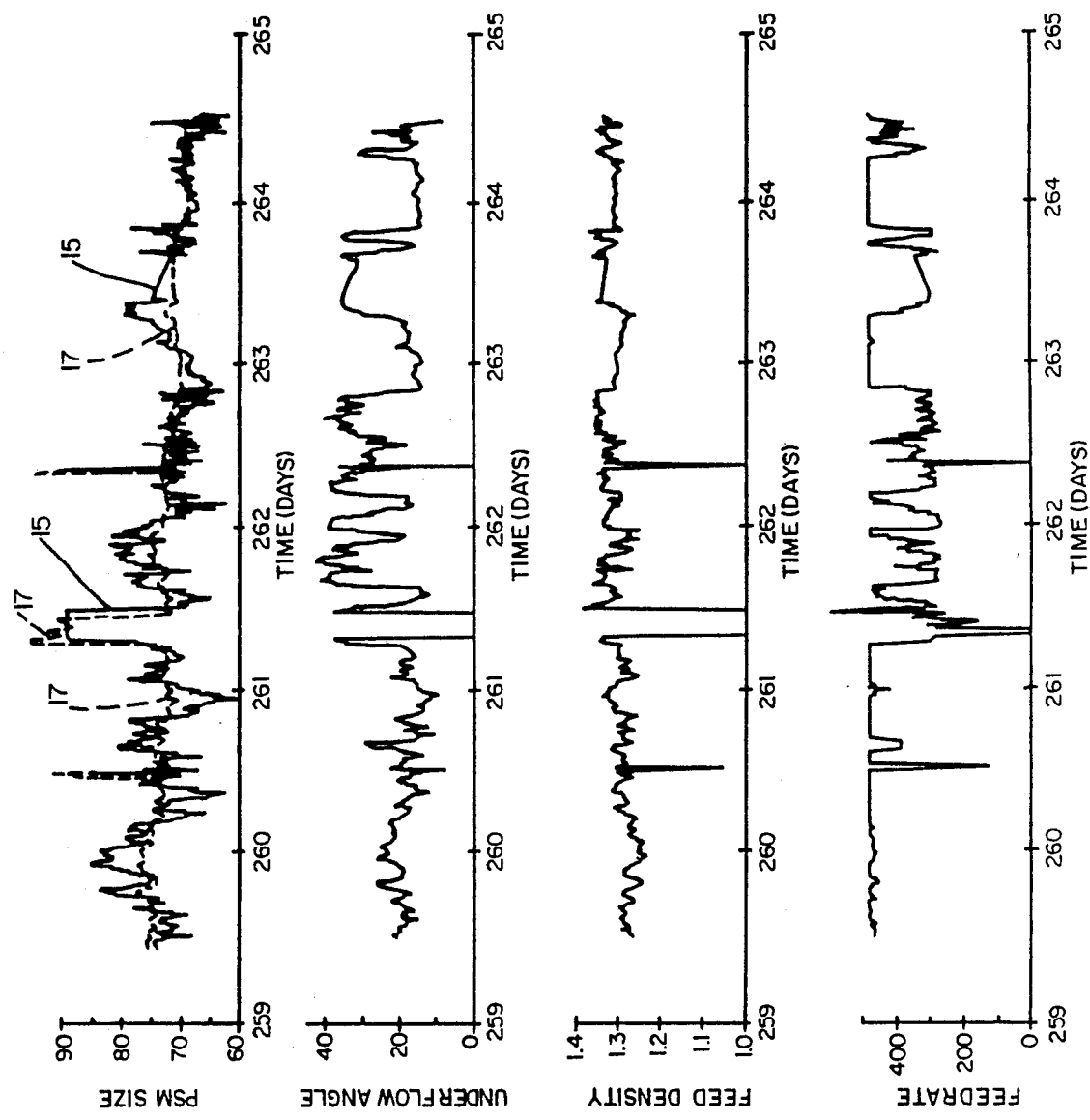

Referring now to FIGS. 3 and 4, there are reproduced a set of recorded charts over a period of five days reflecting four different variables. In each case the upper chart reflects the particle size (as represented by the percentage of material less than 75 $\mu m$), the second chart represents a signal linearly related to the angle of the underflow slurry stream; the third chart reflects the feed density as independently determined by conventional techniques, and the lowermost chart reflects a feed rate as determined by conventional techniques.

In the case of FIG. 3, the upper chart, reflecting particle size, has two separate lines reflected thereon. The one (shown solid) indicated by numeral 15 reflects the actual measured particle size derived from a conventional particle size monitor and the other line (shown dotted) and indicated by numeral 16 shows the particle size derived using a measurement according to the invention. This modelled line 16, obtained according to the invention, was obtained by plotting a course, according to the best model fitted, which applicant was able to derive, which resulted in the formula:

Size = 0.58 × angle − 115 × density + 0.020 × feed rate − 201.

It will be noted that the modelled line fits the measured line extremely well on average and, indeed, it is considered to be more than adequately close enough to the actual measured values to be employed as a control means or for any other practical purpose.

Compared to this, there is shown in FIG. 4, and where the underflow angle of this invention was not employed, a modelled line 17. This line was developed by the best fit that could be obtained according to the formula Size = 50 × density − 0.018 × feed rate + linear drift.

It can be seen that the latter modelled line is substantially inferior to that shown in FIG. 3, particularly where relatively small changes in the particle size are measured. Clearly the derivation of the modelled particle size following the expedient of this invention is far superior. In reality this means that the angle of the underflow slurry stream can be employed instead of a particle size monitor thereby providing an extremely simple piece of equipment to replace an extremely costly automatic particle size monitor.

It will accordingly be appreciated that the invention provides an extremely simple method and means for measuring characteristics associated with any of the feed, underflow or overflow streams of a hydrocyclone which can be used, if required, for control purposes but may be used for other purposes.

Numerous variations may be made to the application of the invention described above without departing from the scope hereof. In particular the measured characteristic may be any of the variable characteristics of the streams, in particular those identified in the summary to the invention, and the means for monitoring the shape of the underflow stream can be varied widely. In particular, the latter means could be other lever arrangements, optionally pivoted to rotate about an axis passing transversely through the axis of the hydrocyclone, or any contactless methods such as electromagnetic radiation, for example light and laser beams, in conjunction with shadowing, attenuation, reflection or any form of imaging process, as well as any position detection utilising ultrasonics.

Still more particularly, it is within the ambit of this invention that a dedicated hydrocyclone be employed for determining characteristics of a slurry stream fed to it and the invention therefore includes within its ambit a particle size monitor as well as other measurement apparatus comprising the aforementioned monitoring means and processor together with a hydrocyclone which may be of small size if used purely for measurement purposes.

What I claim as new and desire to secure by Letters Patent is:

1. A method of measuring a characteristic relating to particle size or particle density of particles in a feed stream leading to a hydrocyclone, in an underflow stream leading from the hydrocyclone, or in an overflow stream leading from the hydrocyclone, the hydrocyclone having an outlet through which the underflow stream exits the hydrocyclone, the method comprising the steps of:

measuring a flow rate of the feed stream;

measuring a density of the feed stream;

measuring a substantially continuously variable quantity of the underflow stream at a predetermined distance from the outlet, the measuring of the variable quantity being performed over a substantially continuous operating range, wherein the step of measuring the variable quantity includes causing a substantially abrasion-resistant element to operatively ride on an outer boundary region of the underflow stream;

processing measurements derived from the measuring of the flow rate, the measuring of the density, and the measuring of the variable quantity; and providing at least one value of the characteristic, based on the processing;

wherein the three measuring steps are performed substantially simultaneously.

2. The method of claim 1, wherein the processing step includes:

using a formula so as to calculate the value of the characteristic.

3. The method of claim 1, wherein the processing step includes:

using an algorithm so as to calculate the value of the characteristic.

4. The method of claim 1, wherein the processing step includes:

using a empirically derived formula or algorithm so as to calculate the value of the characteristic.

5. The method of claim 1, wherein the providing step includes:

providing a value related to the size of particles contained in the feed stream.

6. The method of claim 1, wherein the providing step includes:

providing a value related to the size of particles contained in the overflow stream.

7. The method of claim 1, wherein the providing step includes:

providing a value related to the size of particles contained in the underflow stream.

8. The method of claim 1, wherein the providing step includes:

providing a value related to a range of sizes of particles contained in the feed stream.

9. The method of claim 1, wherein the providing step includes:

providing a value related to a range of sizes of particles contained in the overflow stream.

10. The method of claim 1, wherein the providing step includes:

providing a value related to the range of sizes of particles contained in the underflow stream.

11. The method of claim 1, wherein the providing step includes:

providing a value related to the proportion of particles in at least one of the feed stream, underflow stream and overflow stream, having a size greater than a predetermined size.

12. The method of claim 1, wherein the providing step includes:
providing a value related to the proportion of particles in at least one of the feed stream, underflow stream and overflow stream, having a size less than a predetermined size.

13. The method of claim 1, wherein the step of measuring the variable quantity includes:
measuring a radius of the underflow stream at a predetermined distance away from the underflow outlet.

14. The method of claim 1, wherein the step of measuring the variable quantity includes:
causing a substantially abrasion-resistant element to operatively ride on an outer boundary region of the underflow stream so as to measure the angle, fluctuations in angle, radius, or diameter of the underflow stream.

15. The method of claim 1, wherein the step of measuring the variable quantity includes:
using at least one substantially abrasion-resistant element carried at the end of at least one respective downwardly extending moveable arm, to measure the angle, fluctuations in angle, radius, or diameter of the underflow stream.

16. The method of claim 1, wherein the providing step includes:
providing a value relating to the solids content of the underflow stream.

17. The method of claim 1, wherein the providing step includes:
providing a value relating to the solids content of the overflow stream.

18. The method of claim 1, wherein the providing step includes:
providing a value relating to the flowrate of solids in the underflow stream.

19. The method of claim 1, wherein the providing step includes:
providing a value relating to the flowrate of solids in the overflow stream.

20. The method of claim 1, wherein the providing step includes:
providing a value relating to the flowrate of water in the underflow stream.

21. The method of claim 1, wherein the providing step includes:
providing a value relating to the flowrate of water in the overflow stream.

22. The method of claim 1, further comprising the step of:
controlling operation of the hydrocyclone by using the at least one value provided in the providing step.

23. The method of claim 1, further comprising the step of:
controlling operation of a circuit embodying the hydrocyclone by using the at least one value provided in the providing step.

24. The method of claim 1, wherein the step of measuring the substantially continuously variable quantity includes:
measuring an angle of the underflow stream.

25. The method of claim 1, wherein the step of measuring the substantially continuously variable quantity includes:
measuring a fluctuation in angle of the underflow stream.

26. The method of claim 1, wherein the step of measuring the substantially continuously variable quantity includes:
measuring a radius of the underflow stream.

27. The method of claim 1, wherein the step of measuring the substantially continuously variable quantity includes:
measuring a diameter of the underflow stream.

28. An apparatus arranged for measuring a characteristic related to particle size or particle density of particles in a feed stream leading to a hydrocyclone, in an underflow stream leading from the hydrocyclone, or in an overflow stream leading from the hydrocyclone, the hydrocyclone having an outlet through which the underflow stream exists the hydrocyclone, the apparatus comprising:
flow rate measuring means for measuring a flow rate of feed material in the feed stream;
density measuring means for measuring a density of the feed material in the feed stream;
underflow measuring means for measuring a substantially continuously variable quantity of the underflow stream at a predetermined distance from the underflow outlet, the underflow measuring means measuring the variable quantity over a substantially continuous operating range, wherein the underflow measuring means includes an abrasion-resistant element position so as to operatively ride on an outer boundary of the underflow stream; and
processing means, connected to and for processing measurements provided by the flow rate measuring means, the density measuring means, and the underflow measuring means, the processing means including means for calculating and providing at least one value of the characteristic based on the processing;
wherein the flow rate measuring means, the density measuring means, and the underflow measuring means measure the flow rate of feed material in the feed material in the feed stream, the density of the feed material in the feed stream and the variable quantity of the underflow stream, respectively, substantially simultaneously.

29. The apparatus of claim 28, wherein:
the means for calculating includes means for applying a formula or algorithm to calculate the value of the characteristic.

30. The apparatus of claim 28, wherein:
the means for calculating includes means for applying an empirically derived formula or algorithm to calculate the value of the characteristic.

31. The apparatus of claim 28, wherein:
the calculating means includes means for calculating a value related to the particle size in the underflow stream.

32. The apparatus of claim 28, wherein:
the calculating means includes means for calculating a value related to the particle size in the underflow stream.

33. The apparatus of claim 28, wherein:
the calculating means includes means for calculating a value related to the particle size in the overflow stream.

34. The apparatus of claim 28, wherein the underflow measuring means includes:
a substantially downwardly extending moveable arm having an abrasion-resistant element at a lower end thereof, the abrasion-resistant element positioned so as to operatively ride on an outer boundary of the underflow stream.

35. The apparatus of claim 28, wherein the underflow measuring means includes:
means for measuring an angle of the underflow stream.

36. The apparatus of claim 28, wherein the underflow measuring means includes:
means for measuring a fluctuation in angle of the underflow stream.

37. The apparatus of claim 28, wherein the underflow measuring means includes:
means for measuring a radius of the underflow stream.

38. The apparatus of claim 28, wherein the underflow measuring means includes:
means for measuring a diameter of the underflow stream.

39. A particle size or particle density measuring apparatus, comprising:
a hydrocyclone;
a feed stream leading to the hydrocyclone;
an overflow stream leading to the hydrocyclone;
an underflow stream leading from the hydrocyclone, the hydrocyclone having an outlet through which the underflow stream exits the hydrocyclone;
flow rate measuring means for measuring a flow rate of feed material in the feed stream;
density measuring means for measuring a density of the feed material in the feed stream;
underflow measuring means for measuring a substantially continuously variable quantity of the underflow stream at a predetermined distance from the underflow outlet, the underflow measuring means measuring the variable quantity over a substantially continuous operating range, wherein the underflow measuring means includes an abrasion-resistant element positioned so as to operatively ride on an outer boundary of the underflow stream; and
processing means, connected to and for processing measurements provided by the flow rate measuring means, the density measuring means, and the underflow measuring means, the processing means including means for calculating and providing at least one value of particle size or particle density based on the processing;
wherein the flow rate measuring means, the density measuring means, and the underflow measuring means measure the flow rate of feed material in the feed material in the feed stream, the density of the feed material in the feed stream and the variable quantity of the underflow stream, respectively, substantially simultaneously.

40. The apparatus of claim 39, wherein the underflow measuring means includes:
means for measuring an angle of the underflow stream.

41. The apparatus of claim 28, wherein the underflow measuring means includes:
means for measuring a fluctuation in angle of the underflow stream.

42. The apparatus of claim 39, wherein the underflow measuring means includes:
means for measuring a radius of the underflow stream.

43. The apparatus of claim 39, wherein the underflow measuring means includes:
means for measuring a diameter of the underflow stream.

* * * * *